(12) United States Patent
Verman et al.

(10) Patent No.: US 6,389,100 B1
(45) Date of Patent: *May 14, 2002

(54) X-RAY LENS SYSTEM

(75) Inventors: Boris Verman, Troy; Licai Jiang, Rochester Hills; Bonglea Kim, Troy, all of MI (US); Karsten Dan Joensen, Copenhagen (DK)

(73) Assignee: Osmic, Inc., Auburn Hills, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/289,493

(22) Filed: Apr. 9, 1999

(51) Int. Cl.$^7$ ................................................ G21K 1/06
(52) U.S. Cl. ........................................ 378/84; 378/85
(58) Field of Search .............................. 378/84, 85, 73, 378/147, 148, 156, 145, 82, 34; 350/613; 250/272, 280

(56) References Cited

U.S. PATENT DOCUMENTS

| | | | |
|---|---|---|---|
| 2,853,617 A | | 9/1958 | Berreman |
| 3,032,656 A | | 5/1962 | Hosemann et al. |
| 3,631,249 A | * | 12/1971 | Friede ........................ 378/156 |
| 3,898,455 A | * | 8/1975 | Furnas, Jr. .................. 250/280 |
| 3,927,319 A | | 12/1975 | Wittry |
| 4,028,547 A | * | 6/1977 | Eisenberg ................... 250/272 |
| 4,203,034 A | * | 5/1980 | Carroll, Jr. .................... 378/84 |
| 4,461,018 A | | 7/1984 | Ice et al. |
| 4,525,853 A | | 7/1985 | Keem et al. |
| 4,599,741 A | | 7/1986 | Wittry |
| 4,643,951 A | | 2/1987 | Keem et al. |
| 4,675,889 A | | 6/1987 | Wood et al. |
| 4,693,933 A | | 9/1987 | Keem et al. |
| 4,716,083 A | | 12/1987 | Eichen et al. |
| 4,717,632 A | | 1/1988 | Keem et al. |
| 4,724,169 A | | 2/1988 | Keem et al. |
| 4,727,000 A | | 2/1988 | Ovshinsky et al. |
| 4,777,090 A | | 10/1988 | Ovshinsky et al. |
| 4,783,374 A | | 11/1988 | Custer et al. |
| 4,785,470 A | | 11/1988 | Wood et al. |
| 4,867,785 A | | 9/1989 | Keem et al. |
| 4,940,319 A | * | 7/1990 | Ueda et al. .................. 350/613 |

(List continued on next page.)

FOREIGN PATENT DOCUMENTS

EP 0670576 9/1995

OTHER PUBLICATIONS

Hohlwein, D. et al., "A Graphite Double–Crystal Monochromator for X–Ray Synchrotron Radiation," Journal of Applied Crystallography, vol. 21, pt. 6, pp. 911–915, Dec. 1, 1988.

Pareschi, G. et al., "Bragg Telescopes Based on Polymeric Materials for Hard X–Ray (>10keV) Astronomy," Proceedings of the 8$^{th}$ GIFCO Conference –Cosmic Physics in the Year 2000, Scientific Perspectives and New Instrumentation, pp. 65–69, 1997.

Gambaccini M., et al., "Quasi–Monochromatic X–Ray Source for Mammography Via Crystal Array," Medical Imaging 1997: Physics of Medical Imaging, San Jose, California, Feb. 23–25, 1997 –Proceedings of the SPIE –The International Society for Optical Engineering, vol. 3032, pp. 154–160, 1997.

Banerjee, R. L. et al., "Seeman–Bohlin Linkage for Siemens X–Ray Diffractometer," Review of Scientific Instruments, vol. 62, No. 4, pp. 986–988, Apr. 1991.

Primary Examiner—Robert H. Kim
Assistant Examiner—Irakli Kiknadze

(57) ABSTRACT

A modular x-ray lens system for use in directing x-rays comprising a radiation source which generates x-rays and a lens system which directs the x-rays, wherein the x-ray lens system may be configured to focus x-rays to a focal point and vary the intensity of said focal point.

30 Claims, 7 Drawing Sheets

U.S. PATENT DOCUMENTS

| | | | |
|---|---|---|---|
| 4,958,363 A | | 9/1990 | Nelson et al. |
| 5,001,737 A | * | 3/1991 | Lewis et al. ................. 378/147 |
| 5,027,377 A | | 6/1991 | Thoe |
| 5,082,621 A | | 1/1992 | Wood |
| 5,167,912 A | | 12/1992 | Wood |
| 5,195,115 A | * | 3/1993 | Schiller et al. ................ 378/73 |
| 5,210,779 A | * | 5/1993 | Vali et al. ..................... 378/84 |
| 5,384,817 A | | 1/1995 | Crowther et al. |
| 5,592,338 A | | 1/1997 | Citterio |
| 5,594,773 A | * | 1/1997 | Tomie ........................ 378/145 |
| 5,604,782 A | | 2/1997 | Cash, Jr. |
| 5,646,976 A | | 7/1997 | Gutman |
| 5,684,852 A | | 11/1997 | Tomie |
| 5,745,547 A | * | 4/1998 | Xiao ........................... 378/84 |
| 5,757,882 A | | 5/1998 | Gutman |
| 5,761,256 A | * | 6/1998 | Inoue et al. ................... 378/84 |
| 5,787,146 A | * | 7/1998 | Giebeler ...................... 378/82 |
| 5,799,056 A | | 8/1998 | Gutman |
| 5,880,467 A | * | 3/1999 | Martinis et al. ............. 250/310 |
| 5,982,562 A | * | 11/1999 | Rode .......................... 359/726 |
| 6,041,099 A | | 1/2000 | Gutman et al. |
| 6,014,423 A | | 3/2000 | Gutman et al. |
| 6,069,934 A | | 5/2000 | Verman et al. |

* cited by examiner

X-RAY LENS SYSTEM

BACKGROUND OF THE INVENTION

The present invention relates to an x-ray focusing system. More specifically the present invention relates to a modular system of lenses designed to focus high energy x-rays.

There are various applications which may benefit from the use of focused x-rays. The following background and description illustrate applications of the present invention which are merely exemplary in nature and are in no way intended to limit the invention or its uses. Moreover, the following description, while depicting an x-ray lens system designed to be used in medical applications and crystal diffraction applications, is intended to adequately teach one skilled in the art to make and use the present invention in a variety of x-ray applications, including, but not limited to x-ray structural analysis and x-ray spectroscopy.

Presently, medical applications such as radiotherapy use collimated x-rays for the destruction of malignant tissue. Radiotherapy is one of the major methods, sometimes the only method, in treating some types of cancers such as brain tumors. Linear accelerator systems generating x-rays have been widely used in radiotherapy in the destruction of such malignancies. Linear accelerator systems employed in radiotherapy generally use a multi-leaf collimator to create a shaped beam of x-rays. The shaped x-ray beam intensity has a flux density consistent throughout its extent. The energy range of x-rays generated by such a system usually reach into the MeV range to be effective. To destroy a tumor the linear accelerator system must be continually directed at and rotated about the targeted malignant tissue. The high energy (MeV) of linear accelerator systems and their collimated rays expose a large amount of healthy tissue surrounding a tumor to a potentially damaging concentration of x-rays in the MeV range. The focused x-ray beam of the present invention provides a high brightness focal spot of lower energy x-rays which is used to treat a target in an accurate controlled fashion, as well as treat the target at an early stage. Lower energy x-rays have quicker fall-off behind the target and therefore reduce tissue damage to some sensitive organs which may be exposed to x-rays.

A system utilizing the x-ray focusing properties of the present invention can achieve the same results with reduced damage to collateral tissue and an energy use in the 40 KeV–100 KeV range. The advantages of using this focusing system include: reduced exposure and damage of healthy body tissue to x-rays, the x-rays in the KeV range can be focused directly at a malignancy with decreasing radiation intensity surrounding the x-ray focal point/treatment area, eliminating damage to sensitive organs proximate the target, the energy of the x-rays can be set above the absorption edge of certain materials such as drugs that are delivered to the tumor; the treatment of very small tumors can be done in a more precise manner; and there is an overall lower cost of the present invention as compared with previous linear accelerator systems.

The x-ray focusing properties of the present invention may also be used in the study of crystal structures. A common method used to study crystal structures is x-ray diffraction. The method is based on illuminating a sample crystal with a beam of x-rays. A portion of the x-ray beam is not able to travel directly through the sample crystal, rather some rays are deflected or diffracted and emerge from the sample at varying angles. The incident x-rays make their way along the spaces between the atoms of the crystal or are deflected by the atoms. A sensor is used which detects the x-ray diffraction pattern generated by the x-rays as they emerge from the sample crystal. This diffraction pattern corresponds to the atomic structural arrangement of the crystal. Such a system is known in the art as an x-ray diffractometer. The focusing properties of the present invention can improve the flux concentration on a sample crystal leading to improved diffraction patterns.

Many devices can be used to focus, and/or reflect x-rays such as total reflection mirrors, bent single crystals, graded multi-layer devices, and mosaic crystals. The main purpose of these devices is to gather Y-ray flux produced by an x-ray generator and direct it to a desired area. There are three main factors which determine the flux strength of a reflecting and focusing device: reflection angle, reflectivity, and rocking curve width. Reflection angle is the angle at which x-rays are reflected from the surface of the reflection surface, reflectivity is the amount of energy returned from a surface after x-rays are incident upon that surface, and rocking curve width is the ability to collect and reflect energy over a particular incident range.

The total reflection mirror has the smallest reflection angle of all the previously mentioned devices, which results in the smallest capture angle and in turn, small throughput, although its reflectivity approaches 100%. The total reflection mirror will also reflect the desired and undesired x-ray wavelengths. In medical applications, these undesired x-ray wavelengths could potentially cause skin damage to a person undergoing treatment.

Bent single crystals have a large reflection angle and high peak reflectivity but a very narrow bandpass limiting the gathered flux to a small amount.

Multi-layered x-ray reflectors have a fairly wide rocking curve width and high peak reflectivity. The reflection angle is also larger than a total reflection mirror. The reflectivity and rocking curve width will drop when smaller d-layer spacing is used to achieve larger reflection angles. For high energy x-rays, such as in the multiple 10 KeV range, the x-ray focusing efficiency of the multi-layer reflector is not satisfactory.

Mosaic crystals consist of numerous tiny independent crystal regions which are nearly parallel but not quite parallel to one another. Mosaic crystals such as a graphite crystal have high reflectivity, a large reflection angle, and therefore a large capture angle. Mosaic crystals also have a large rocking curve width due to their mosaic structure. All of these factors make the mosaic crystal an attractive choice for reflecting and directing high energy x-rays. The focusing lenses of the present invention are composed of mosaic crystals such as a graphite crystal.

SUMMARY OF THE INVENTION

The present invention is a modular system of lenses used for focusing x-rays. The lenses are operated using the principles of Bragg reflection and Laue diffraction. The ideal crystal surfaces and crystal planes of these lenses follow the Johansson scheme. In practice, cylindrical, conical, even polygonal surfaces can be used for approaching the focusing scheme. The lenses using Bragg diffraction deliver a beam of narrow frequency band (substantially monochromatic) x-rays, while the lenses using Laue diffraction deliver a controlled wide frequency band of x-rays. Many lenses can be designed to have the same source-focal point distance. Each of the lenses has different source-lens and lens-focus distances, depending on the requirements of focal spot size, working distance (front end of the lens to focal point), and flux, different lenses or combinations of several lenses can be used. This modularity creates a simple yet flexible scheme for varying intensity, focal spot size, and working distance.

The lenses utilizing Bragg reflection use mosaic graphite crystal on their inner surfaces arranged in a cylindrical configuration. The lenses are formed by the bending of graphite layers or alternatively the direct growth of graphite on a lens housing. Graphite was chosen as preferred mosaic crystal in the Bragg lenses because of its superior reflective properties. The Laue lenses utilizing a Laue transmission scheme are similarly comprised of mosaic graphite crystal, but the x-rays are transmitted and diffracted through the crystal volume rather than being reflected only from the incident surface of the mosaic graphite crystal.

For many applications, different focal spot sizes and different intensities are needed for varying flux density requirements. These requirements can be met by the use of supplementary Bragg reflective x-ray lenses with internal spherical, cylindrical, conical, parabolic, ellipsoid or other conic type configuration, but are not limited to such configurations. These supplementary x-ray lenses can be used to collect x-rays and focus them at varying focal lengths and create varying focal point areas and intensities. This modularity creates a simple yet flexible scheme of varying the intensity, focal length, and focal point area of an x-ray beam.

DETAILED DESCRIPTION OF THE PREFERRED EMBODIMENT

Figure 1:
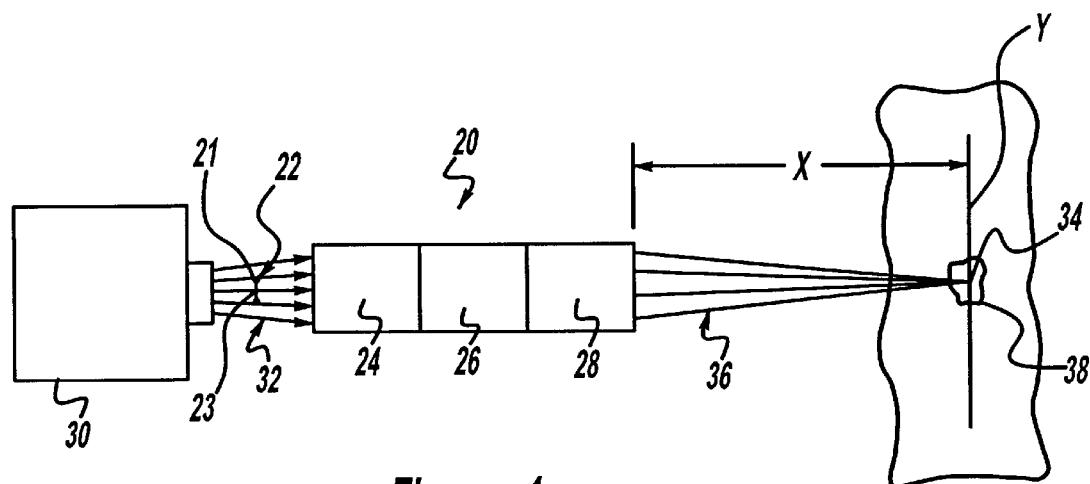
FIG. 1 is a diagrammatic view of an x-ray system utilizing the lens system of the present invention.

FIG. 1 is a diagrammatic an x-ray system utilizing the lenses of the present invention. The x-ray lens system is generally shown as 20 in this present embodiment and includes an x-ray filter 22, lens 24, a main lens 26, and an extension lens 28. The present invention may be used with only one of these lenses or any combination of these lenses or other lenses defined in this description. An x-ray generator 30 produces x-rays 32 which include direct or coaxial x-rays that are filtered by x-ray filter 22. The x-ray filter 22, which may be a bandpass, highpass or lowpass filter, is comprised of a ring 21 which blocks or absorbs off-axis x-rays that are not reflected by the interior of the lenses and/or do not converge to the focal point 34 of the lens system 20. A filtering medium 23 is placed within the ring 21 of the x-ray filter 22 to filter x-rays entering the lens system 20, bypassing the reflective surfaces of the lens system 20, and traveling directly to focal point 34. Alternatively, the filter 22 may be placed at the exit aperture of a lens system 20 or two filters 22 may be used simultaneously at both the entrance and exit apertures of a lens system 20.

The x-rays 32 are collected by the x-ray lens system 20 and focused by the lens system 20 as x-rays 36 which converge to focal point 34. In radiotherapy, a system utilizing the x-ray focusing properties of the present invention can destroy a malignancy with reduced damage to collateral tissue and an energy use in the KeV range rather than the MeV range. This use of lower energy x-rays allows quicker fall-off behind the target tissue and reduced damage to tissue located behind the target tissue. A malignancy or target volume 38 is subjected to the greatest intensity of the focused x-rays 36 when the focal point 34 of the lens system is placed directly upon the malignancy 38. This focusing action also minimizes the radiation exposure of the healthy tissue surrounding the malignancy, decreasing collateral damage to the healthy tissue. The modular nature of the lens system 20 is evidenced by the ease at which the focal length and focal point area is adjusted. The focal length X and focal point 34 area of the x-ray lens system is easily changed by substituting different individual lens components with lenses of the desired aspect combinations. The focusing properties of the present invention also lead to the advantages of having improved flux and resolution in x-ray diffraction or other x-ray applications.

Figure 2:
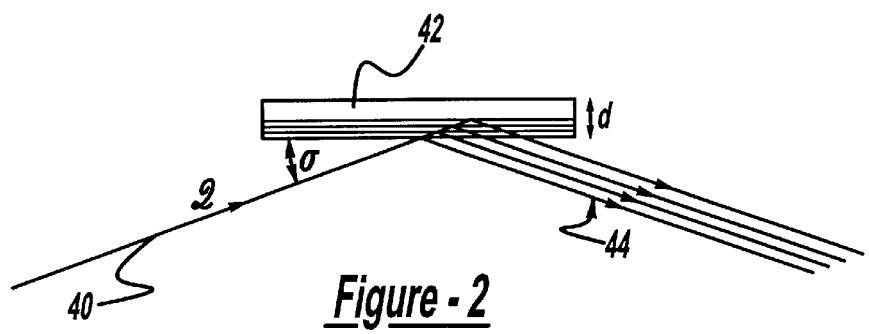
FIG. 2 is a diagram of a simple Bragg reflector.

The x-ray lenses of the present invention utilize the principles of Bragg reflection and Laue diffraction. FIG. 2 provides a graphical illustration of a simple Bragg reflector. X-ray radiation 40 of wavelength $\lambda$ is incident on a crystal or multilayer 42 having lattice or multilayer spacing d. Narrow band or generally monochromatic radiation 44 is than reflected according to Bragg's Law. Mosaic graphite is the preferred crystal structure which may be utilized as a Bragg reflector to provide a narrow band or generally monochromatized x-ray beam. In other embodiments other crystals or Bragg structures such as multilayers can be substituted within the lens system to reflect radiation using Bragg's law. Mosaic graphite and other Bragg structures only reflect radiation when Bragg's equation is satisfied:

$$n\lambda = 2d\sin(\theta)$$

where
n=the order of reflection
λ=wavelength of the incident radiation
d=layer-set spacing of a Bragg structure or the lattice spacing of a crystal
θ=angle of incidence Mosaic graphite was chosen as the preferred x-ray reflecting or diffracting material in the embodiments of the present invention because of its superior performance properties, such as a large reflection angle, large rocking curve width due to the mosaic structure, and high reflectivity. In both Bragg and Laue diffraction, Bragg's law dictates the reflection and/or diffraction of the incident x-rays. The only difference is in Bragg diffraction the incident and diffracted beam share the same crystal surface, while in the Laue case the incident and diffracted beam use two different surfaces. The former is usually called a "reflection scheme" and the latter is referred to as a "transmission scheme".

The structure of the mosaic graphite consists of a regular three dimensional array of atoms which forms a natural diffraction grating for x-rays. The quantity d in Bragg's equation is the perpendicular distance between the planes of atoms in the mosaic graphite forming the diffraction grating. Mosaic crystal consists of numerous tiny independent crystal regions which are nearly parallel but not quite parallel with one another. When x-rays from an x-ray source strike a reflective surface the incidence angle varies since the point of reflection of various x-rays are at differing distances from an x-ray source. As the incidence angle of x-rays falling upon the mosaic graphite is varied so will the crystal regions reflecting the x-rays. This is caused by the differing orientations of the individual crystal regions within the mosaic graphite. There is not only an incidence angle upon the general surface of the mosaic graphite but individual local incidence angles upon the independent crystal regions. An x-ray beam falling on the mosaic graphite will reflect at a wider incident angle than a perfect crystal because x-rays entering into the graphite at wider incident angles will reach mosaic elements oriented correctly for reflection at that angle. The mosaic graphite reflects over an angular range which depends on the scatter of the mosaic orientations but the range is greater than that of a perfect crystal or multi-layered thin film Bragg reflector.

Figure 3:
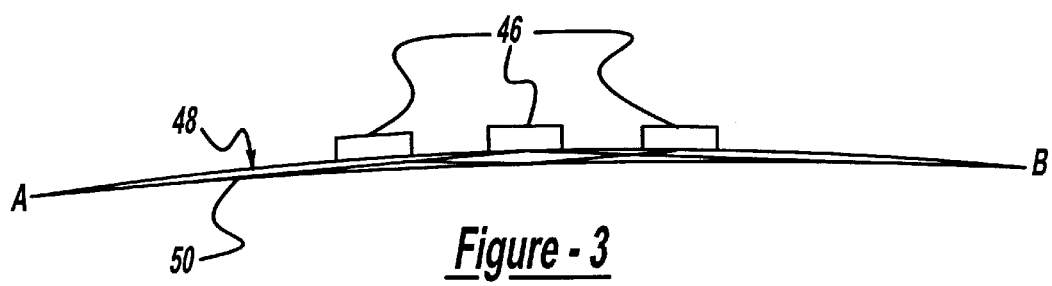
FIG. 3 is a diagrammatic view of the crystal regions in mosaic carbon reflecting x-rays.

The arrangement of the lattice structure and crystal regions may be varied from slightly ordered to highly ordered depending on the application. For x-rays of differing energy, the Bragg angle is different and mosaicity provides the capability to accept more energy over a wider angular range. In the preferred embodiment, the main parameters of the graphite used in the Bragg reflective lenses of the present invention are:

d-spacing d: 3.33 Å
FWHM w: 0.5°
Reflectivity R.: 50%
Density ρ: 2.25 g/cm$^3$
Attenuation $\mu$: 0.175 g$^{-1}$·cm$^2$ FIG. 3 is a diagrammatic view of the crystal regions 46 in mosaic carbon reflecting x-rays. The reflecting surface 48 of the Bragg lens is curved in a circular manner. This curvature will improve the focusing properties of the lens by keeping the incident angle constant for x-rays that are incident throughout the extent of reflecting surface 48. This ideal reflective surface will allow x-rays 50 generated at point A and incident upon individual crystal regions 46 to be focused at point B. The individual crystal regions 46 are shown slightly out of parallel with respect to each other resulting in the focal point B. The Bragg condition is guaranteed by the following two conditions, the angle made by an incident x-ray and reflected x-ray is constant along the circle and the tiny crystal regions will make correct Bragg angle exits. For crystal with different d-spacings, and different source-focus point a different size circle will be chosen to meet the Bragg angle requirements. In a real application, x-rays might meet proper crystal regions not exactly on the circle due to using flat crystals. This will give a widened beam spot on focal point B. The parallelism and performance of a mosaic crystal reflector is characterized and described completely by its rocking curve width, its inherent reflectivity, and attenuation coefficient.

Figure 4:
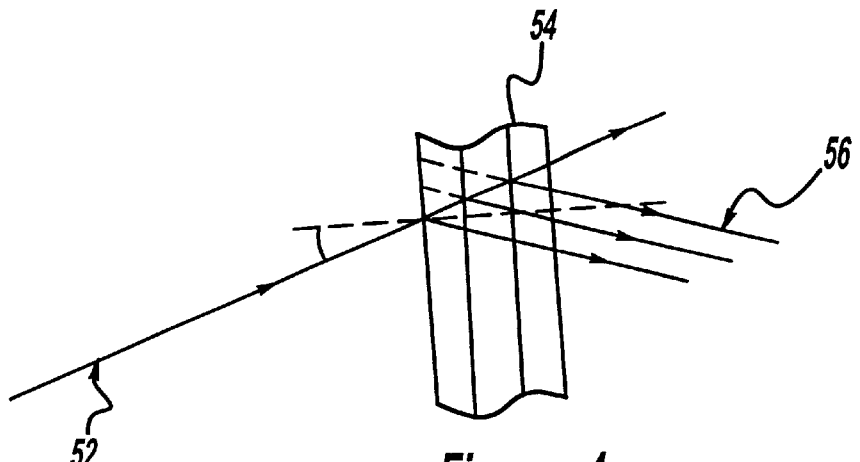
FIG. 4 is a diagrammatic view of Laue x-ray diffraction in an x-ray lens.

In further embodiments of the present invention, the principle of Laue diffraction/transmission is utilized to direct and focus x-rays. As seen in FIG. 4, incident x-rays 52 penetrate a crystal 54 and a portion of the incident x-rays 52 is diffracted and travels through the crystal 54 along the diffracted direction and exits the crystal 54 as focused x-rays 56. In a Laue lens configured as a ring, x-rays are diffracted at different focusing circles within the crystal. The Bragg angles are different at different point in the crystal volume, which results in an overall wider spectrum than Bragg reflectors.

Figure 5:
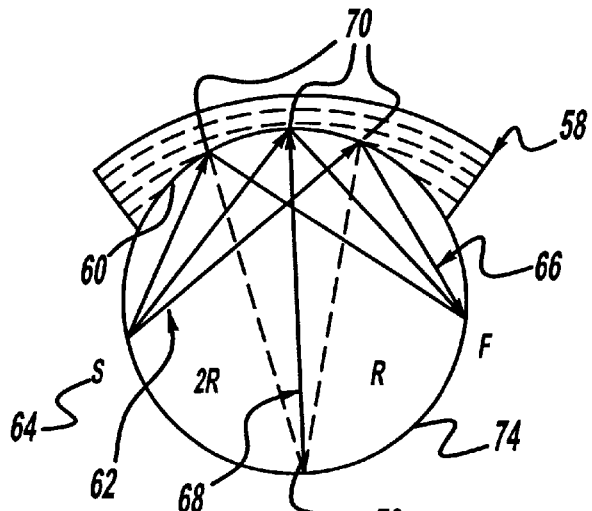
FIG. 5 is a diagram of the bent Johansson crystal working principle.

The ideal inner mosaic graphite crystal surfaces and crystal planes of the lenses of the present invention follow the Johansson scheme. As seen in FIG. 5, a bent Johansson crystal 58 is used to reflect and focus x-rays. The bent Johansson crystal 58 will reflect x-rays according to Bragg's law. The Johansson crystal 58 is made by bending a crystal into a cylindrical surface with a normal radius 2R, and then polishing the reflection surface 60 to a cylindrical surface with radius R. The angle made by each pair of incident rays 62 generated by x-ray source 64 and reflected rays 66 is the same. The lines 68 that connect reflection points 70 to the point 72 on the other side of the circle 74, which is the symmetric point to the source and the focal point, are always equal and bi-partition the angle. Therefore, the curve that is perpendicular to these lines will constitute a Bragg plane, which are the bent 2R crystal planes in this Figure.

Figure 6:
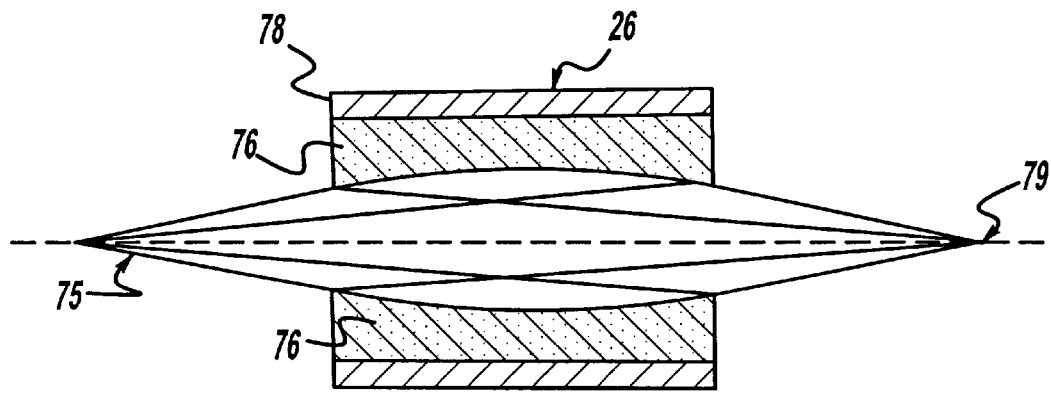
FIG. 6 is a lengthwise cross sectional view of the main lens of the present invention focusing x-rays and having a curved reflective surface with respect to incident x-rays.

FIG. 6 is a perspective of the main x-ray lens 26 used in the present invention. The main x-ray lens 26 is cylindrical in form with a hollow interior lined with a graphite layer 76. Preformed or "bent" graphite blocks can be bonded together to form the graphite layer 76 on the interior of a lens housing 78. In one embodiment of the present invention four graphite blocks, each covering a quarter of the interior of the x-ray lens 26, are mounted on the interior of the x-ray long 26 to form a curved interior surface. In an alternate configuration graphite can be grown by deposition process inside the lens housing 78 to form a reflection layer.

In the preferred embodiment of the present invention, as seen in FIG. 6, the mosaic graphite layer 76 will approximate the reflecting surface of the Johansson Crystal illustrated in FIG. 5. The surface of the interior of the main x-ray lens 26 will be curved in a circular manner relative to the housing and incident x-rays 75. The term circular is used when referring to a Gross section or two-dimensional picture of the lens system, but a person of ordinary skill in the art would recognize that in three dimensions the lenses would be curved relative to the housing. This curving results in a smaller focal point area, as the mosaic graphite crystal will be aligned in the ideal form of the Johansson crystal to improve the focusing properties of the main x-ray lens 26

Figure 7:
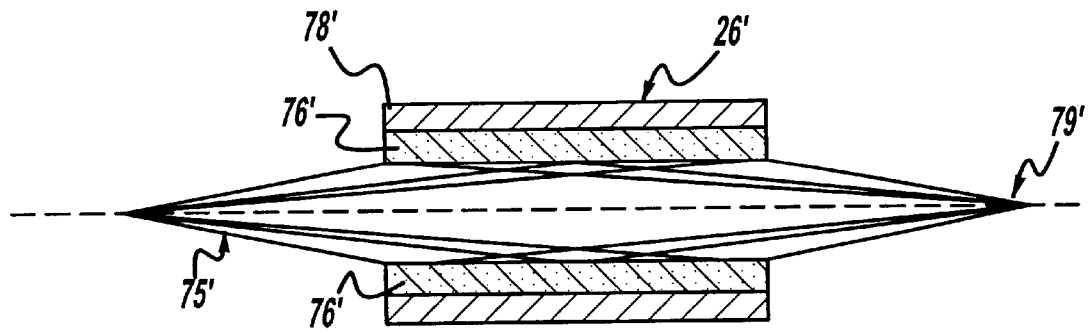
FIG. 7 is a lengthwise cross sectional view of the main lens of the present invention focusing x-rays and having a flat reflective surface with respect to incident x-rays.

FIG. 7 is a lengthwise cross sectional view of an alternate embodiment of the main Bragg reflective lens 26' of the present invention focusing x-rays. The main Bragg reflective lens 26', as shown by the drawing, has a graphite layer 76' that is not inclined or angled, rather it is substantially concentrically flat relative to the cylindrical housing of the main lens 78' relative to incident x-rays 75'. The barrel or interior surface of the main lens 26' therefore has generally a constant inner diameter throughout its full length. The flat reflecting surface of the graphite layer 76' is easier to fabricate than the curved graphite surface 76 shown in FIG. 6 and will roughly approximate the surface of a the Johansson crystal shown in FIG. 5. The focusing properties of flat reflecting surface of the graphite layer 76' will have more aberration than the curved graphite surface 76, shown in FIG. 6 of the leading to a larger focal point 79'.

Figure 8:
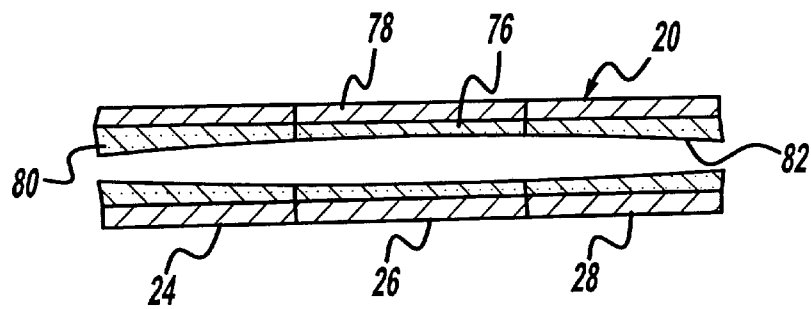
FIG. 8 is a lengthwise cross sectional view of a multiple x-ray lens system of the present invention having curved surfaces with respect to incident x-rays.

FIG. 8 is a cross sectional view of a modular x-ray lens system of the present invention. The lens system 20 can be constructed from a plurality of lens components. In the present embodiment, the lens 24 is coupled to the main lens 26 which further couples to an extension lens 28 to focus x-rays. The lenses may be coaxially physically coupled by threaded members, flanges or other connection devices known in the art. The lenses are preferably in a cylindrical configuration. The inner mosaic graphite crystal surfaces 80, 76 and 82 of these lenses follow the Johansson scheme shown in FIG. 5 when adjacent to each other. The mosaic graphite surfaces have been configured to approximate the ideal Johansson crystal reflecting shape. As discussed previously, the term circular is used when referring to a cross section or two dimensional picture of the lens system, but a person of ordinary skill in the art would recognize that in three dimensions the lenses would be curved. The modularity of the system is also beneficial. The focal point and x-ray intensity of the present invention can be varied by simply arranging, removing, or adding lenses with various reflecting characteristics. Multiple combinations of individual lenses can be configured to meet almost any application.

Figure 9:
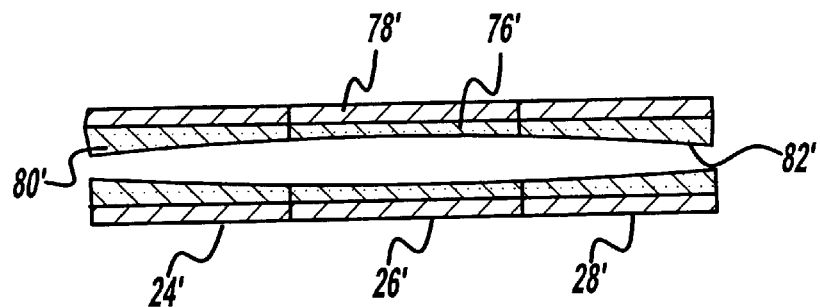
FIG. 9 is a lengthwise cross sectional view of a multiple x-ray lens system of the present invention having flat and angled surfaces with respect to incident x-rays.

Referring to FIG. 9, the mosaic graphite layer 80' of lens 24' is sloped in linear fashion (conical in three dimensions), the mosaic graphite layer 76' of main lens 26' is flat (cylindrical in three dimensions), and the mosaic graphite layer 82' of extension lens 28' is also sloped in linear fashion (conical in three dimensions) opposite to that of mosaic graphite layer 80'. These lenses alone do not possess a curved shape but when placed together approximate the curved circular shape of the ideal reflective surface of the Johansson crystal with their angular and flat surfaces. This conical system is also modular and lenses may be added or removed to improve performance.

The main performance of an x-ray lens is its collecting and transmitting capability for x-rays. It can be described by throughput which is defined as the solid angle from the source, which contains the same amount of photons the lens delivers to the focal point. If we define a solid angle which extends 1° in both directions, as a unit for the throughput, this unit will be equal to:

$$\text{unit throughput} = \int_{89.5°}^{90.5°} \sin\theta\, d\theta \int_{0}^{0.01745} d\phi = 3.05 \times 10^{-4} \text{ strad}$$

All Bragg reflective lenses in this section will be estimated in this unit.

The parameters of the main lens 26' are:
Inner diameter: 25 mm
Length: 115 mm
Source-lens center distance: 400 mm
Lens center-focus distance: 400 mm
Capture angle: 1.70×10⁻³ strad
Focal spot size: 2–4 mm
Throughput 2.78

The wavelength of an x-ray at 60 KeV is calculated from the following formula:

$$\lambda = \frac{12.4}{E(\text{keV})} = \frac{12.4}{60} = 0.207 \text{ Angstroms}$$

The Bragg angle is:

$$\theta = \sin^{-1}\left(\frac{\lambda}{2d}\right) = \sin^{-1}\left(\frac{0.207}{2\times 3.33}\right) = 1.779°$$

The capture angle will be determined by:

$$\Delta\Omega = \int_{1.529°}^{2.029°} \sin\theta\, d\theta \int_{0}^{2\pi} d\phi = 1.70 \times 10^{-3} \text{ strad}$$

In the case of the main lens 26', the throughput is equal to the capture angle multiplied by the average reflectivity. Therefore the throughput is 8.5×10⁻⁴ strad. In the unit defined above, the throughput of our lens 26' will be 2.78.

The parameters of the lens 24' are:
Inner diameter of the exit: 25 mm
Inner diameter of the entrance; 23.5 mm
Length: 86.5mm
Source-lens center distance: 299 mm
Lens center-focus distance: 501 mm
Capture angle: 2.18×10⁻³ strad
Focal spot size: 4–10 mm, depending on source size
Throughput 3.57

The capture angle will be determined by:

$$\Delta\Omega = \int_{2.029°}^{2.529°} \sin\theta\, d\theta \int_{0}^{2\pi} d\phi = 2.18 \times 10^{-3} \text{ strad}$$

As discussed above, the throughput is equal to the capture angle multiplied by the average reflectivity. Therefore the throughput is 1.09×10⁻³ strad and in the unit defined above, the throughput of the lens 24' will be 3.57. The lens 24' will give a large throughput, but will generate a larger focal spot.

The parameters of the extension lens 28' are:
Inner diameter of the exit: 23.5 mm
Inner diameter of the entrance: 25 mm
Length: 86.5 mm
Source-lens center distance: 501 mm
Lens center-focus distance: 299 mm
Capture angle: 1.22×10⁻³ strad
Focal spot size: depends on source size
Throughput 1.97

The capture angle will be determined by:

$$\Delta\Omega = \int_{1.026°}^{1.526°} \sin\theta\, d\theta \int_{0}^{2\pi} d\phi = 1.22 \times 10^{-3} \text{ strad}$$

The throughput is 0.61×10⁻⁴ strad and in the unit defined above, the throughput of lens 28' will be 1.97. The extension lens 28' has finer focus and larger convergent angle.

The intensity distribution and throughput of a particular combination of lenses can be calculated based on source information, source projection size, intensity distribution, etc.

Figure 10:
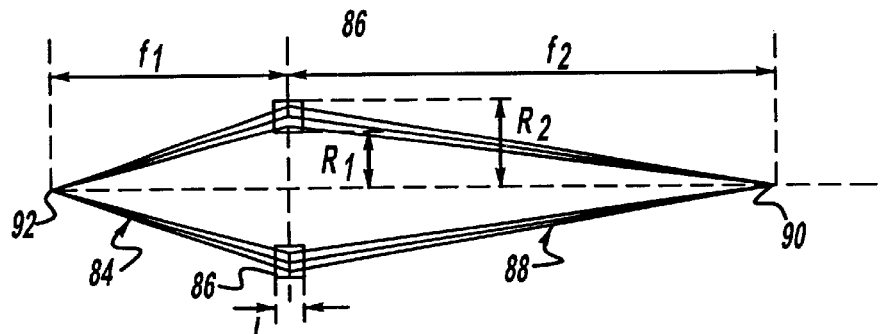
FIG. 10 is a diagrammatic view of an x-ray lens of the present invention utilizing the principle of Laue x-ray diffraction.
Figure 11:
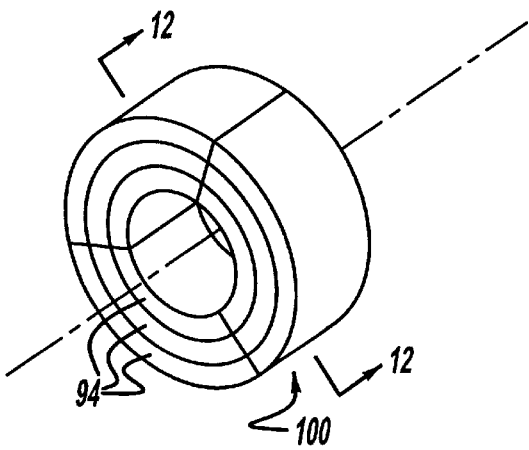
FIG. 11 is a perspective view of an x-ray lens of the present invention comprised of multiple concentric layers of mosaic graphite crystal.

In further embodiments of the present invention, Laue diffraction/transmission lenses are utilized to direct and focus x-rays. Referring to FIG. 10, a Laue lens 86 of the present invention is illustrated. Incident x-rays 84 penetrate the Laue lens or crystal 86 (in a ring configuration) and a portion of the x-rays 84 is diffracted and travels through the lens 86 along the diffracted direction and exits the lens 86 as focused x-rays 88. In Laue diffraction, x-rays are diffracted at different focusing circles within the crystal. The Bragg angles are different at different points in the crystal volume, which results in an overall wider spectrum than Bragg reflectors. The x-rays 84 are reflected from each lattice layer and directed towards a focal point 90. The distance between the source 92 and the lens 86 is $f_1$ and the distance between the lens 86 and the focal point 90 is $f_2$. The length of the lens is L. The inner diameter of the Laue lens 86 is $R_1$ and the outer diameter is $R_2$.

In the case where $f_1$ is not equal to $f_2$, the direction of the atomic planes of the Laue lens 86 will need to change along the diameter direction. Otherwise, the x-rays will not be reflected to the desired focal point. With $f_1=f_2$, the lens will be a flat ring instead of a tilted ring with varying atomic planes. Following are two designs; one has symmetric design, and the other has asymmetric design. They have the same working distance and different focal spot size. The main reason for the asymmetric design is to conserve materials and reduce the overall dimension of the system.

In the symmetric design, the performance parameters of the graphite for Laue reflection are the same as for Bragg reflection, except for the reflectivity. As measured recently by Applicants, it is about 18% around 60 KeV.

d-spacing d: 3.33 ○

FWHM w: 0.4 ◊(24 arc minutes)

Laue reflectivity R: <18%

Density ρ: 2.25 g/cm³

Attenuation $\mu$: 0.175 g⁻¹·cm²

The following is a particular design of a Laue lens 86 for the performance estimation. The main parameters of the lens 86 are listed below:

Inner diameter: 16.3 mm

Outer diameter: 32.6 mm

Length: variable

Source-lens center distance: 350 mm

Lens center-focus distance: 350 mm

The inner edge of the Laue lens 86 is tuned to work at 80 KeV; and the outer edge is tuned to work at 40 KeV. The band pass at each point is given by $$\Delta E = \frac{E\cos\theta \cdot \Delta\theta}{\sin\theta}$$

At the position where the incident angle θ, the energy of the x-rays which satisfy the Bragg law is $$E = \frac{12.4}{2d\sin\theta}$$

Therefore the band pass as a function of q can be written as $$\Delta E = \frac{12.4\cos\theta \cdot \Delta\theta}{2d\sin^2\theta}$$

where Δθ is the rocking curve width.

The capture angle will be determined by, $$\Delta\Omega = \int_{\theta_1}^{\theta_2} \sin\theta \cdot d\theta \int_0^{2\pi} d\phi$$

where $\theta_2$ is the incident angle at the outer edge and $\theta_1$ is the incident angle at inner edge.

$$\theta_1 = \sin^{-1}\left(\frac{12.4}{80} \frac{1}{2\times 3.33}\right) = 1.33°$$

$$\theta_2 = \sin^{-1}\left(\frac{12.4}{40} \frac{1}{2\times 3.33}\right) = 2.67°$$

$$\Delta\Omega = \int_{\theta_1}^{\theta_2} \sin\theta \cdot d\theta \int_0^{2\pi} d\phi = 5.13\times 10^{-3} \text{ sterad.}$$

The efficiency of the lens 86 can be written as $$\text{Efficiency} = \int_{\theta_1}^{\theta_2} R\cdot \Delta E \cdot \sin\theta \cdot d\theta \int_0^{2\pi} d\phi = \int_{\theta_1}^{\theta_2} R\frac{12.4\cos\theta \cdot \Delta\theta}{2d\sin\theta} d\theta \int_0^{2\pi} d\phi$$

where R is 0.18 and Δθ=0.4°=0.00698 Rad.

$$\text{Efficiency} = 0.00234 \int_{1.33°}^{2.67°} \frac{\cos\theta}{\sin\theta} d\theta \int_0^{2\pi} d\phi = 0.021$$

$$\text{Throughput} \approx \frac{\text{Efficiency}}{3.05\times 10^{-4}\cdot 40} \approx 0.82$$

In the unit "Effective solid angle" unit, the throughput should be $$\Delta\Omega' \approx 8.2\times 10^{-5}$$

assuming the voltage setting is 120 kV.

The performance summary is:

Capture angle: 5.13×10⁻³ strad

Focal spot size: ~3 mm (depends on fabrication accuracy)

Throughput: 0.82

Effective solid angle: 8.2×10⁻⁵

Figure 12:
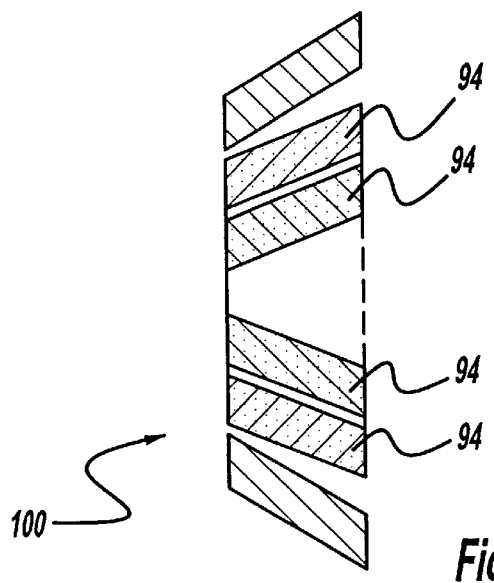
FIG. 12 is a cross sectional view taken along line 12—12 in FIG. 11.

The asymmetric lens design shown in FIG. 12 can save material and shorten assembly time. However, as discussed above, theoretically the tilting angle of each layer 94 is different. In practice, it can be approximated by limited number of crystal layers. Each layer 94 is made of whole piece of crystal. Therefore the tilting angle of the crystal plane is the same within each layer 94.

This particular lens 100 design includes three concentric layers 94 (rings) having a thickness of 2 mm in the preferred embodiment. The inner radius of the lens is 5.4 mm, while the outer radius of the lens is 11.4 mm. Each lens layer 94 has a conical configuration. The main parameters of this design are given in Table 1.

TABLE 1

| Major parameters of the asymmetric design | | | | | |
|---|---|---|---|---|---|
| Object distance (Source-Lens, mm) | | | | | 180 |
| Image distance (Lens-focal plane, mm) | | | | | 350 |
| Rings | ID (mm) | OD (mm) | Energy (KeV) | Conical Angle (°) | Graphite (mm³) |
| Inner | 10.8 | 14.8 | 60~80 | 0.50 | 46.5 × 10 × 2* |
| Middle | 14.8 | 18.8 | 47~60 | 0.65 | 59 × 10 × 2* |
| Outer | 18.8 | 22.8 | 40~47 | 0.80 | 71.6 × 10 × 2* |

Figure 13:
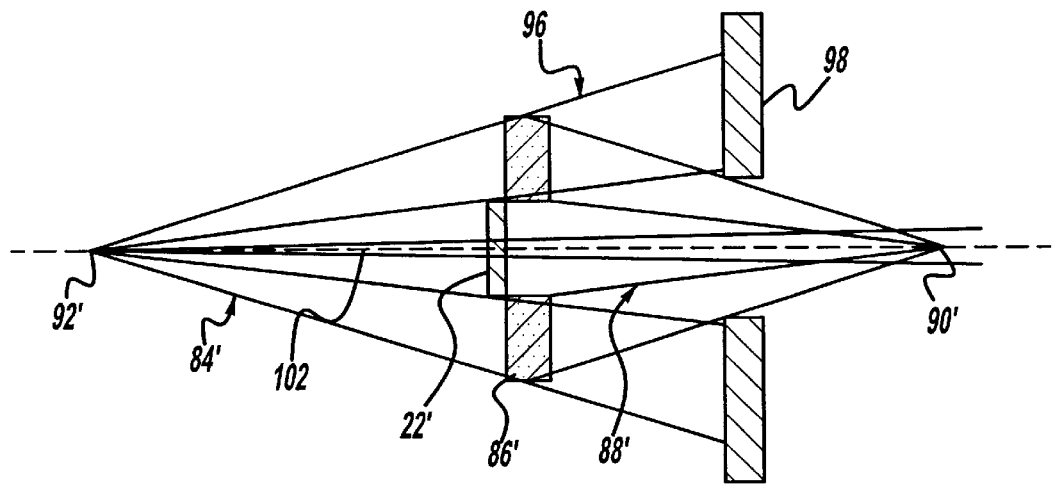
FIG. 13 is a cross sectional view of an x-ray lens of the present invention utilizing the principle of Laue x-ray diffraction and equipped with beam stoppers and filters.

Referring to FIG. 13, a further embodiment of the present invention is shown utilizing Laue reflection to focus x-rays. An x-ray source 92' directs x-rays 84' to the lens or crystal 86' where some of the x-rays 88' are diffracted and focused and transmitted x-rays 96 exit the crystal without being diffracted. Beam stopper 98 blocks these transmitted x-rays 96. Coaxial x-rays 102 will be filtered by x-ray filter 22' similar to the previously described x-ray filter 22.

Figure 14:
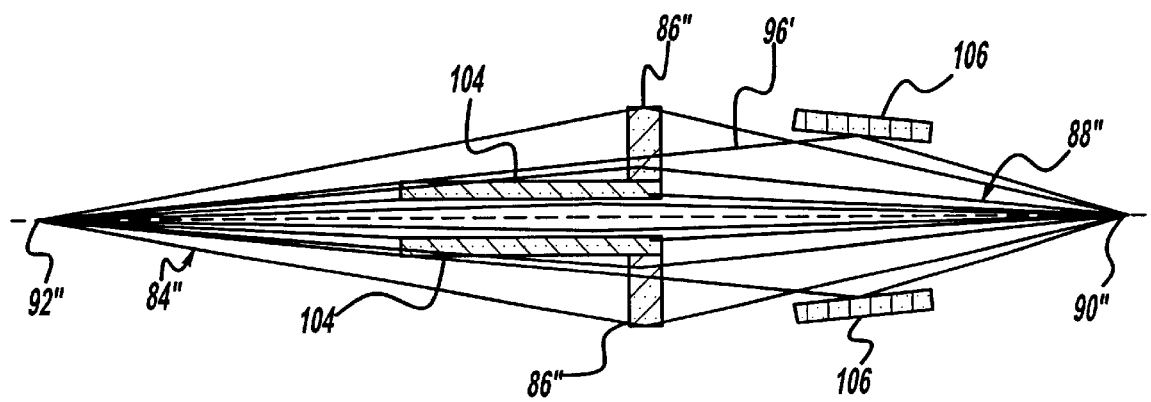
FIG. 14 is a cross section view of a combination x-ray lens utilizing the principles of Laue x-ray diffraction and Bragg x-ray reflection.

A cross section of a combination Laue and Bragg lens system is illustrated by FIG. 14. The x-ray source 92" directs a portion of the x-rays 84" to a Bragg reflective surface 104, preferably comprised of mosaic graphite crystal, which reflects generally monochromatic x-rays to the focal point 90". A portion of the x-rays 84" also are directed to the graphite crystal 86" where some of the x-rays 88" are diffracted and focused to a focal point 90". Transmitted x-rays 96' which travel through the crystal 86" are incident upon a second Bragg reflective surface or lens 106 configured to focus the transmitted x-rays 96' to focal point 90". This configuration of multiple Bragg and Laue lenses increases the flux concentrating power of the combination lens system. X-rays which were previously occluded or blocked ore now conditioned and directed towards focal point 90".

The graphite reflecting and diffraction layers of the x-ray lenses of the present invention may be formed by a variety methods including but not limited to direct growth on a lens housing and the bending of a generally flat graphite sheet. The bending process will allow the creation of a conical graphite lens at room temperature.

Figure 15:
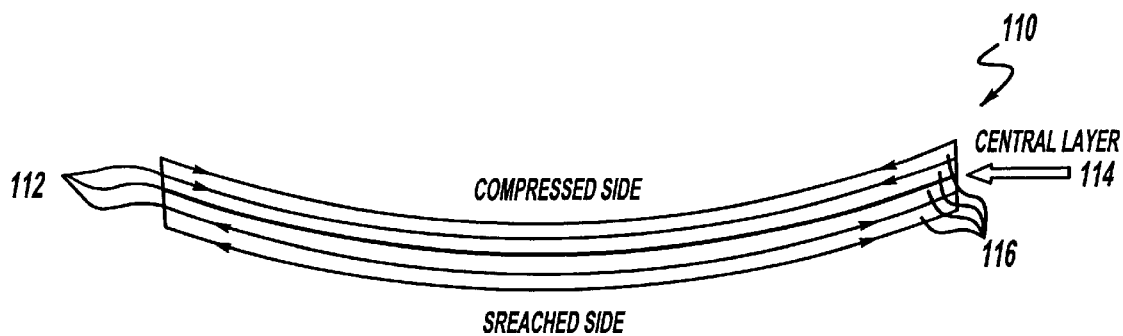
FIGS. 15–17 illustrate the methods of bending graphite used to fabricate the x-ray lenses of the present invention.
Figure 16:
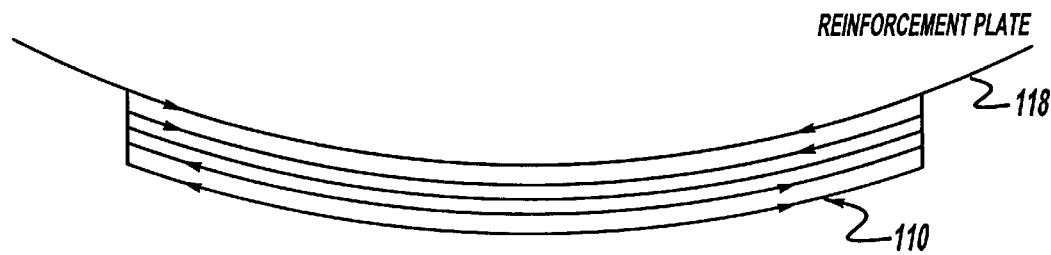
Figure 17:
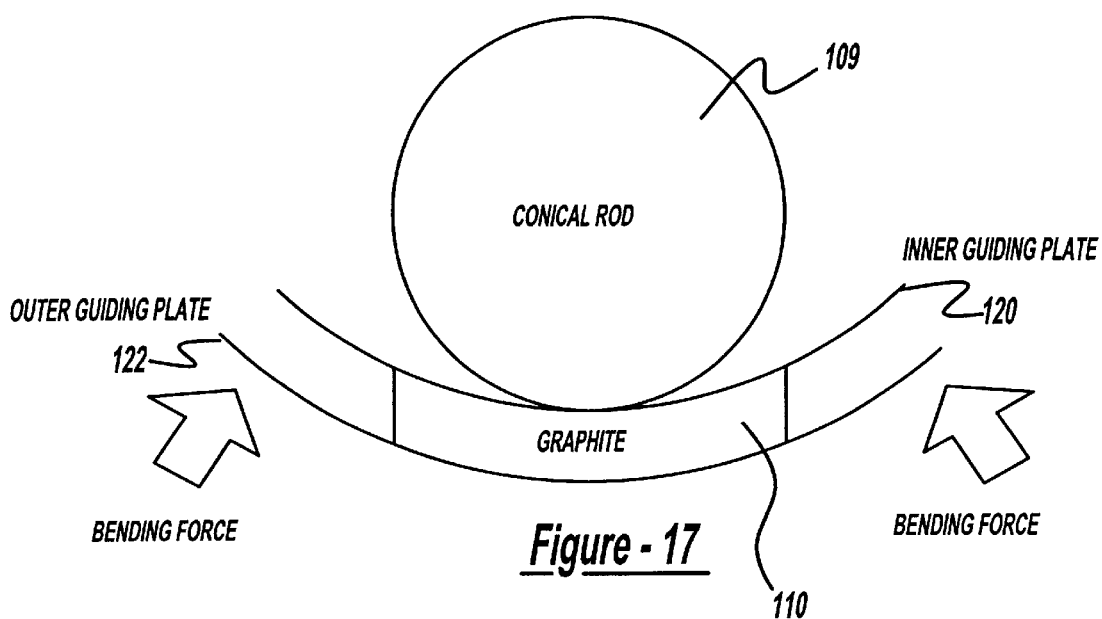

Referring to FIGS. 15–17, in one embodiment of the present invention a generally conical lens is formed by the bending of four identical plates 110 of graphite, each bent plate 110 representing a quarter of the lens, i.e. ninety degrees. The bent plates 110 are assembled in a housing to create the complete conical lens. The quality of bending will directly affect the performance of a graphite lens since the positive stress (compressing force) along the layer direction during bending will damage the mosaicity of the graphite. For example, as shown in FIG. 15, there are three different layers 112 of stress if a graphite lens is bent without a supporting structure. The central layer 114 undergoes no stress during bending. Below and above this central layer the graphite layers 116 will experience negative and positive stresses. The magnitude of the stress is linearly proportional to the distance from the central layer 114 and the length of the graphite plate 110. Damage to the mosaicity of the graphite is directly related to positive stress.

In order to minimize the damage to the graphite plate 110 during the bending procedure, three methods of bending may be used. In the first method, since a shorter graphite plate will experience lesser stress during the bending process, several bent graphite plates 110 can be used to form a complete circle as seen in the previous embodiments of the invention. The number of graphite plates 110 to be segmented depends on the radius of the graphite plate 110, thickness of the graphite plate 110 and the mechanical properties of the graphite plate 110. In the second bending method, as shown in FIG. 16, a reinforcement plate 118 is introduced to shift the zero-stress layer to the front surface of the graphite plate 110. In the preferred embodiment, the reinforcement plate 118 is comprised of a piece of transparent mylar sheet glued or affixed onto the front surface of the graphite sheet 110 before bending. The reinforcement plate 118 is removed after bending in order to expose the front surface of the graphite plate 110 to the environment. In the third method, as seen in FIG. 17, two guiding plates 120 and 122 are used to guide the graphite plate 110 for uniform bending.

In the third method shown in FIG. 17, a conical rod 109 is placed on the inner guiding plate 120 and the graphite plate 110 is sandwiched by inner guiding plate 120 and outer guiding plate 122. The bending forces are applied to the graphite plate 110 through the guiding plates 120 and 122 so that the graphite plate 110 will form along the conical rod 109 and assume the shape of the conical rod 109.

Figure 18:
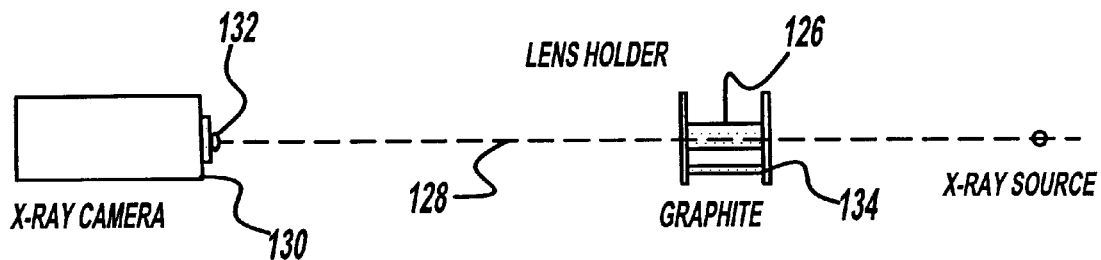
FIG. 18 illustrates the calibration of an x-ray lens and lens holder.

There are two methods for lens assembly to be used in the present invention. FIG. 18 shows a first method of lens mounting where individual bent graphite lens segments are assembled into a complete lens. The axis 128 of a lens holder 126 defines the axis of the lens system. The x-ray camera 130 is positioned at the focal point 132. The position and the angles of an individual bent graphite plate 134 are adjusted such that the reflected beam is focused on the focal point 132. The bent graphite plate 134 is fixed to the holder 126 after the alignment. All remaining graphite plate segments are mounted onto the holder 126 with this procedure.

Figure 19:
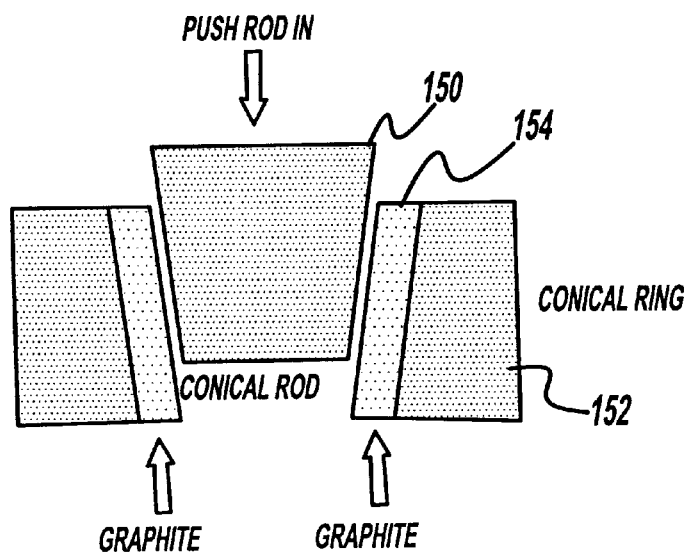
FIG. 19 illustrates the method of forming a conical surface for the lenses of the present invention.

Referring to FIG. 19, another method of lens assembly using a conical ring 152 and a conical rod 150 formed with the desired conical angles is illustrated. All bent graphite plates 154 are assembled simultaneously in this single ring lens method. One or more spacers are needed to fill the gap caused by different conical angles between layers for a multi-layer lens system. The inner rod 150 and the spacers are made from a material with less x-ray absorption than the bent graphite plates 154 and enough mechanical strength and chemical stability to withstand the bending forces generated by the conical rod 150.

It is to be understood that the invention is not limited to the exact construction illustrated and described above, but that various changes and modifications may be made without departing from the spirit and scope of the invention as defined in the following claims.

What is claimed is:

1. An x-ray system for directing x-rays comprising:

a lens system which directs said x-rays, wherein said lens system comprises at least one lens element comprising a housing with a generally enclosed interior, said interior of said housing lined with a Bragg x-ray diffraction and reflection layer and said housing does not reflect said x-rays, wherein said Bragg x-ray diffraction and reflection layer comprises a mosaic crystal comprising a curved cross section lengthwise and said mosaic crystal comprises a curved crystal plane with a differing radius from that of said curved cross section.

2. The x-ray system of claim 1, wherein said Bragg x-ray diffraction and reflection layer comprises a mosaic crystal.

3. The x-ray system of claim 1, wherein said Bragg x-ray diffraction and reflection diffracts and transmits said x-rays.

4. The x-ray system of claim 1, wherein said interior of said lens element comprises a widthwise circular cross section.

5. The x-ray system of claim 1, wherein said interior of said lens element comprises a conical cross section lengthwise.

6. The x-ray system of claim 1, wherein said lens system comprises a plurality of lens elements coupled coaxially.

7. The x-ray system of claim 1, wherein said lens system focuses said x-rays to a focal point.

8. The x-ray system of claim 1 further comprising a beam stopper, wherein said beam stopper blocks said x-rays which are not directed towards a focusing region.

9. The x-ray system of claim 8, wherein said beam stopper blocks unreflected x-rays which are transmitted through said lens system.

10. An x-ray system for direting x-rays comprising:
a lens system which direct said x-rays, wherein said lens system comprises at least one lens element comprising a housing with a generally enclosed interior, said interior of said housing lined with a Bragg x-ray diffraction and reflection layer;
wherein said lens system comprises a plurality of lens elements coupled along their symmetric axis and said coupled lens elements do not overlap one another in a direction perpendicular to their symmetric axis.

11. The x-ray system of claim 10, wherein said plurality of lens elements generally form a Johansson crystal reflecting surface.

12. An x-ray system for directing x-rays comprising:
a lens system which directs said x-rays, wherein said lens system comprises at least one lens element comprising a housing with a generally enclosed interior, said interior of said housing lined with a Bragg x-ray diffraction and reflection layer and said housing does not reflect said x-rays; and
a ring-like apparatus comprising a filter medium coupled to a center of said ring-like apparatus, wherein said ring-like apparatus occludes a portion of said x-rays which are not incident upon said lens system and do not fall into a focusing region of said lens system, said filter medium filtering a portion of said x-rays which is directed to said focusing region.

13. An x-ray system for focusing x-rays comprising:
a modular lens system comprising a plurality of lenses which collect said x-rays and focus said x-rays to a focal point, wherein x-ray focusing properties of said modular lens system can be varied by removing and adding said plurality of lenses or changing the properties of said plurality of lenses.

14. The x-ray system of claim 13, wherein said x-ray focusing properties are selected from the croup consisting of:
x-ray spectrum bandpass;
working distance;
flux strength
focal spot size, and
focal length.

15. The x-ray system of claim 13 wherein each of said plurality of lenses comprises a housing comprising a Bragg x-ray diffractive and reflective layer.

16. The x-ray system of claim 15, wherein said Bragg x-ray diffractive and reflective layer comprises a mosaic crystal.

17. The x-ray system of claim 15, wherein said Bragg x-ray diffractive and reflective layer comprised graphite.

18. The x-ray system of claim 15, wherein each of said plurality of lenses comprises an interior surface comprising a lengthwise curved cross section.

19. The x-ray system of claim 15, wherein each of said plurality of lenses comprises an interior surface comprising a widthwise circular cross section.

20. The x-ray system of claim 15, wherein at least one of said plurality of lenses comprises an interior surface comprising a lengthwise conical cross section.

21. The x-ray system of claim 15, wherein at least one of said plurality of lenses comprises an interior surface comprising a lengthwise rectangular cross section.

22. The x-ray system of claim 15, wherein said plurality of lens elements are coupled coaxially.

23. The x-ray system of claim 15, wherein said plurality of lens elements are coupled along an x-ray source-focus axis.

24. The x-ray system of claim 15, wherein said plurality of lens elements have inner surfaces which generally form a Johansson crystal reflecting surface.

25. An x-ray lens system comprising:
a plurality of lenses, each of said plurality of lenses comprising a housing comprising an inner surface lined with graphite,
an x-ray filter proximate said plurality of lenses, and
wherein said inner surfaces of said plurality of lenses in combination are formed to give said x-ray lens system an interior generally spherical surface.

26. An x-ray system for directing x-rays:
a lens system which directs said x-rays, wherein said lens system comprises at least one lens element comprising a cylindrical housing comprising an interior, said interior of said cylindrical housing lined with a mosaic crystal, whereby said mosaic crystal acts as a Bragg or Laue lens to direct said x-rays, and
a mask for occluding x-rays off axis to said lens system; and
a filter for filtering x-rays substantially coaxial to said lens system and which are directed to a focusing region.

27. The x-ray system of claim 26, wherein said mask occludes x-rays which are not intercepted by said lens system and x-rays which are not deflected towards a focal point of said lens system.

28. An x-ray system for directing x-rays comprising
a lens comprising a Bragg x-ray diffractive layer, wherein said directed x-rays are transmitted and diffracted through said lens;
wherein said lens is constructed from a plurality of concentric rings of mosaic crystal forming a plurality of diffractive layers.

29. The x-ray system of claim 28, wherein said lens comprises a ring configuration.

30. The x-ray lens system of claim 28 further comprising an x-ray filter.

* * * * *

UNITED STATES PATENT AND TRADEMARK OFFICE
CERTIFICATE OF CORRECTION

PATENT NO.    : 6,389,100 B1
DATED         : May 14, 2002
INVENTOR(S)   : Boris Verman et al.

It is certified that error appears in the above-identified patent and that said Letters Patent is hereby corrected as shown below:

Title page,
Item [56], U.S. PATENT DOCUMENTS,
Delete "12/1971" and substitute -- 9/1969 -- in its place.
Delete "7/1985" and substitute -- 6/1985 -- in its place.
Delete "1/2000" and substitute -- 3/2000 -- in its place.
Delete "3/2000" and substitute -- 1/2000 -- in its place.

Column 13,
Line 37, delete "croup" and substitute -- group -- in its place;
Line 40, insert -- ; -- (semicolon) immediately after "flux strength"; and
Line 41, delete "size," and substitute -- size; -- in its place.
Line 45, insert -- , -- (comma) immediately after "claim 13".
Line 52, delete "comprised" and substitute -- comprises -- in its place.

Column 14,
Line 22, delete "graphite," and substitute -- graphite; -- in its place; and
Line 23, delete "lenses," and substitute -- lenses; -- in its place.
Line 43, insert -- : -- (colon) immediately after "comprising".
Line 52, insert -- , -- (comma) immediately after "claim 28".

Signed and Sealed this

Eighteenth Day of March, 2003

JAMES E. ROGAN
*Director of the United States Patent and Trademark Office*